United States Patent [19]

Richard et al.

[11] Patent Number: 5,961,962
[45] Date of Patent: Oct. 5, 1999

[54] PHOTOPROTECTIVE/COSMETIC COMPOSITIONS COMPRISING CINNAMONITRILE-SUBSTITUTED POLYORGANOSILOXANES/ POLYORGANOSILANES

[75] Inventors: Hervé Richard, Villepinte; Madeleine Leduc, Paris; Alain Lagrange, Couvray, all of France

[73] Assignee: Societe L'Oreal S.A., Paris, France

[21] Appl. No.: 09/123,460

[22] Filed: Jul. 28, 1998

Related U.S. Application Data

[62] Division of application No. 08/559,940, Nov. 17, 1995, Pat. No. 5,827,509.

[30] Foreign Application Priority Data

Nov. 17, 1994 [FR] France .................................. 94 13769

[51] Int. Cl.⁶ .............................. A61K 7/42; A61K 7/00; C07F 7/08
[52] U.S. Cl. .................................. 424/60; 424/47; 424/59; 424/70.12; 424/401; 528/41; 528/43; 556/415; 556/416; 556/417
[58] Field of Search ................................ 424/59, 60, 401, 424/47, 70.12; 528/41, 43; 556/415, 416, 417

[56] References Cited

U.S. PATENT DOCUMENTS

| | | | |
|---|---|---|---|
| 5,587,151 | 12/1996 | Richard et al. | 424/59 |
| 5,610,257 | 3/1997 | Richard et al. | 528/15 |
| 5,714,134 | 2/1998 | Richard et al. | 424/59 |
| 5,827,509 | 10/1998 | Richard et al. | 424/60 |

FOREIGN PATENT DOCUMENTS

92/19625  11/1992  WIPO .

OTHER PUBLICATIONS

Journal of Organometallic Chemistry, vol. 285, 1985, pp. 375–381, Fitzmaurice, N. J. et al, "The Stereochemistry of Organometallic Compounds", XXXVI. Regio–and Stereo–Chemical Control in the Nickel–Catalysed Hydrocyanation of Silylalkynes.

*Primary Examiner*—Shelley A Dodson
*Attorney, Agent, or Firm*—Burns, Doane, Swecker & Mathis, L.L.P.

[57] ABSTRACT

Topically applicable sunscreen/cosmetic compositions well suited for enhanced photoprotection of human skin and/or hair against the damaging effects of UV-A and UV-B irradiation, particularly solar radiation, comprise a photoprotecting effective amount of a novel cinnamonitrile-substituted polyorganosiloxane/polyorganosilane.

15 Claims, No Drawings

5,961,962

PHOTOPROTECTIVE/COSMETIC COMPOSITIONS COMPRISING CINNAMONITRILE-SUBSTITUTED POLYORGANOSILOXANES/ POLYORGANOSILANES

CROSS-REFERENCE TO COMPANION APPLICATIONS

This application is a divisional, of application Ser. No. 08/559,940, now U.S. Pat. No. 5,827,509 filed Nov. 17, 1995, the contents of which are incorporated herein by reference.

Our applications Ser. No. 08/541,983 U.S. Pat. No. 5,663,270, filed Oct. 10, 1995, Ser. No. 08/555,334 U.S. Pat. No. 5,569,457 and Ser. No. 08/555,046 U.S. Pat. No. 5,610,257, both filed Nov. 8, 1995], and Ser. No. 08/559,941 now ABN and Ser. No. 08/560,489, U.S. Pat. No. 5,587,151 both filed concurrently herewith; each of the above applications is assigned to the assignee hereof.

BACKGROUND OF THE INVENTION

1. Technical Field of the Invention

The present invention relates to novel compounds comprising short-chain, linear or cyclic diorganosiloxanes or triorganosilanes bearing at least one sunscreening cinnamonitrile substituent bonded thereto via an alkylene or alkyleneoxy bridging group.

This invention also relates to novel cosmetic compositions for topical application comprising said cinnamonitrile-substituted polyorganosiloxanes/polyorganosilanes, for the photoprotection of the skin and/or hair against ultraviolet radiation (such compositions hereinafter sometimes simply designated "sunscreen," "sunscreen/cosmetic" or "photoprotective/sunscreen" compositions).

2. Description of the Prior Art

It is known to this art that light radiation of wavelengths of from 280 nm to 400 nm promotes tanning of the human epidermis, and that irradiation of wavelengths of from 280 to 320 nm, i.e, UV-B irradiation, causes erythema and skin burns which can impair the development of a natural tan; hence, such UV-B radiation must thus be screened from the skin.

It is also known to this art that UV-A radiation, of wavelengths of from 320 to 400 nm, which tans the skin, also adversely affects it, in particular in the event of sensitive skin or skin constantly exposed to solar radiation. UV-A irradiation causes, in particular, a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of compounds intended for the photoprotection (UV-A and/or UV-B) of human skin are known to this art.

Most of these are aromatic compounds displaying an absorption of UV radiation in the region from 280 to 315 nm or in the region of from 315 to 400 nm, or else in both of these regions together. They are, more often than not, formulated in sunscreen compositions as oil-in-water emulsions (namely, a cosmetically acceptable vehicle, carrier or diluent comprising an aqueous continuous dispersing phase and an oily discontinuous dispersed phase) which contain, at various concentrations, one or more traditional lipophilic and/or hydrophilic organic sunscreen compounds comprising an aromatic function suitable for selectively absorbing harmful or deleterious UV radiation. These sunscreen compounds (and the amounts thereof) are selected as a function of the desired specific sun protection factor (the specific protection factor (SPF) being expressed mathematically by the ratio of the irradiation time required to attain the erythemogenic threshold with the UV screening agent to the time required to attain the erythemogenic threshold in the absence of UV screening agent.)

Other than their sunscreen activity, these compounds having anti-UV properties must also display good cosmetic characteristics in the compositions comprised thereof, good solubility in common solvents, and especially fats such as oils and greases, and also good resistance to water and to perspiration (durability). It too is desirable that these sunscreen compositions be nontoxic and do not penetrate into the skin.

Among such prior art aromatic compounds, p-aminobenzoic acid derivatives, benzylidenecamphor derivatives, cinnamic acid derivatives and benzotriazole derivatives are particularly representative. However, certain of these, as well as others of the known sunscreen compounds do not display all of the properties required for an acceptable UV screening agent in sunscreen compositions. In particular, their intrinsic screening activity may be insufficient, ofttimes mandating that relatively large amounts of compound be employed to attain satisfactory screening properties, but at the expense of the cosmetic properties of the ultimate formulations thereof. In addition, their solubility in the different formulations employed for photoprotection is not always sufficiently good (fat solubility in particular), they may not possess sufficient stability to light (photostability) and they may also display poor resistance to water and to sweat.

SUMMARY OF THE INVENTION

Accordingly, a major object of the present invention is the provision of novel cinnamonitrile-substituted silicone/silane sunscreen compounds which display improved properties, and which avoid, or conspicuously ameliorate, the above disadvantages and drawbacks to date characterizing the state of this art.

Thus, it has now unexpectedly been determined that by grafting, in particular via hydrosilylation, one or more specific cinnamonitrile screening derivatives, namely, one or more cinnamonitrile compounds which comprise an alkylene or alkyleneoxy bridging group, to a particular linear or cyclic silicone chain or a particular silane, novel silicone/silane sunscreen compounds are prepared which display, in particular, very high sunscreen activity, both in the UV-A range and in the UV-B range, very good solubility in the common organic solvents and notably in fatty substances such as oils, excellent photostability, and also excellent cosmetic properties, rendering same particularly well suited for formulation into photoprotective/cosmetic compositions for protecting the skin and/or the hair against the damaging or deleterious effects of ultraviolet radiation.

Briefly, the present invention features novel compounds having one of the following formulae (1) to (3):

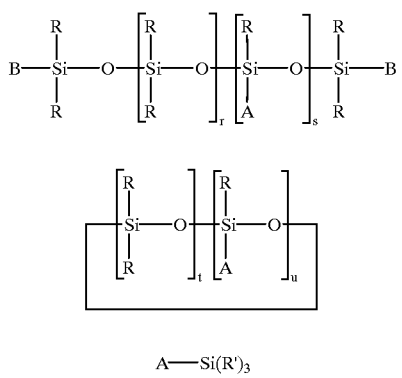

(1)

(2)

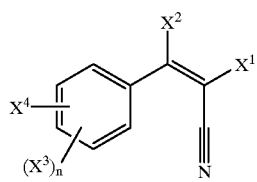

A—Si(R')$_3$ (3)

in which the radicals R, which may be identical or different, are each a $C_1$–$C_{10}$ alkyl, phenyl or 3,3,3-trifluoropropyl radical, at least 80% by number of the radicals R being methyl radicals; the radicals B, which may be identical or different, are each a radical R or a radical A as defined below; the radicals R', which may be identical or different, are each a $C_1$–$C_8$ alkyl radical or a phenyl radical; r is an integer ranging from 0 to 50, inclusive, and s is an integer equal to 0 or 1, with the proviso that, if s is zero, then at least one of the two radicals B is a radical A; t is an integer ranging from 2 to 10, inclusive; and the radical A is a monovalent radical bonded directly to a silicon atom and which has the following formula (4):

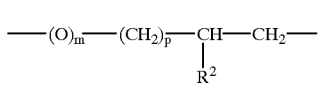

(4)

wherein $X^1$ is a cyano radical or an alkoxycarbonyl radical COOR$^1$ in which the radical R$^1$ is (i) a $C_1$–$C_{20}$ alkyl radical or (ii) a $C_2$–$C_{20}$ hydroxyalkyl radical, or (iii) a divalent radical —Y— having the following formula (5):

$$—(O)_m—(CH_2)_p—CH—CH_2—$$
$$\phantom{—(O)_m—(CH_2)_p—}|$$
$$\phantom{—(O)_m—(CH_2)_p—}R^2$$

(5)

in which $R^2$ is a hydrogen atom or a $C_1$–$C_4$ alkyl radical, p is an integer ranging from 0 to 10, inclusive; m is 0 or 1; the —CH$_2$— endgroup is directly bonded to a silicon atom; $X^2$ is a hydrogen atom or an optionally substituted phenyl or $C_6$–$C_{10}$ aryl radical; n is an integer ranging from 0 to 2, inclusive; the radicals $X^3$, which may be identical or different, are each a $C_1$–$C_8$ alkyl radical or a $C_1$–$C_4$ alkoxy radical, with the proviso that, when the radicals $X^3$ are alkoxy radicals, two adjacent radicals $X^3$ (n=2) may together form an alkylidenedioxy group in which the alkylidene moiety contains 1 or 2 carbon atoms; and $X^4$ is a hydrogen atom or a divalent radical —Y—, with the proviso that, if $X^4$ is a hydrogen atom, then $X^1$ is necessarily a radical COOY in which m is zero.

DETAILED DESCRIPTION OF BEST MODE AND PREFERRED EMBODIMENTS OF THE INVENTION

More particularly according to the present invention, in the above formulae (1) to (3), A is thus the radical derived from the cinnamonitrile which, after bonding to the starting short silicone chain or to the starting silane, imparts absorbing properties to the compounds of linear diorganosiloxane type (formula (1)), or of cyclic diorganosiloxane type (formula (2)), or of triorganosilane type (formula (3)), with respect to ultraviolet radiation within a wavelength region which may range from 280 to 400 nm. As indicated above, and as is apparent from the definition of the above formula (4), this group necessarily comprises at least one alkylene or alkyleneoxy function defining a bridging structural unit which ensures grafting of the cinnamonitrile to the silicone backbone or to the silane. One of the advantages of the compounds according to the invention is that, depending on the nature and/or position of the various substituents borne by the screening nucleus A, either purely UV-A screening agents or, to the contrary, purely UV-B screening agents, are provided, exhibiting particularly high extinction coefficients.

Also as is apparent from the above formula (4), the linking radical —(O)$_m$—(CH$_2$)$_p$—CH(R$^2$)—CH$_2$— (i.e., a divalent radical —Y— of formula (5)) may, according to the present invention, be grafted onto the structural unit derived from the cinnamonitrile, which thus ensures bonding of said structural unit to a silicon atom of the silicone backbone or of the silane, at any one of the available positions capable of being occupied by the radicals $X^1$ or $X^4$, the —(O)$_m$— endgroup of said bridging moiety becoming bonded to the structural unit derived from the cinnamonitrile and its —CH$_2$— endgroup becoming bonded to a silicon atom of the silicone backbone or of the silane.

In the above formulae (1) to (3), the alkyl radicals can be linear or branched and are advantageously selected from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred alkyl radicals R, R' and B according to the invention are methyl, ethyl, propyl, n-butyl, n-octyl and 2-ethylhexyl radicals. Even more preferably, the radicals R, R' and B are all methyl radicals. As regards the alkoxy radicals, these are advantageously selected from among methoxy, ethoxy, n-propoxy, isopropoxy, n-butoxy and isobutoxy radicals.

Among the compounds of the above formulae (1) to (3), preferred are those corresponding to formula (1) or to formula (2), namely, linear or cyclic short-chain diorganosiloxanes.

Among the linear or cyclic diorganosiloxanes according to the present invention, preferred are the random derivatives or well-defined block derivatives having at least one, and even more preferably all, of the following characteristics and definitions:

R is alkyl and, even more preferably, is methyl,

B is alkyl and, even more preferably, is methyl (in the case of the linear compounds of formula (1) ), r ranges from 0 to 6, inclusive; s ranges from 0 to 6, inclusive (in the case of the linear compounds of formula (1)), t+u ranges from 3 to 5 (in the case of the cyclic compounds of formula (2)), $X^1$ is cyano or a radical COOR$^1$ in which R$^1$ is methyl, ethyl or —Y—, $X^2$ is H or phenyl, $X^3$ is methoxy (n≠0) or H (n=0), $X^4$ is —Y—, preferably in position 4 of the ring member, p ranges from 1 to 3, inclusive, $R^2$ is H or methyl.

To prepare the silicone sunscreen agents of formulae (1) and (2), a standard hydrosilylation reaction (Method 1) is employed, i.e.:

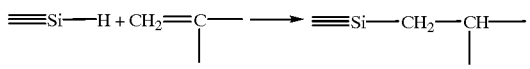

starting from the corresponding silicone in which, for example, all of the radicals A are hydrogen atoms. This starting silicone will hereinafter be designated the derivative containing SiH; the SiH groups may be present in the silicone backbone and/or at the ends of the silicone chain. These derivatives containing SiH are well known compounds in the silicone industry and are widely available commercially. They are described, for example, in U.S. Pat. Nos. 3,220,972, 3,697,473 and 4,340,709.

This derivative containing SiH may thus be represented, depending on the particular case, either by the following formula (1a):

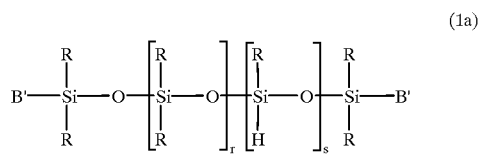

in which R, r and s are as defined above in respect of the formula (1) and the radicals B', which may be identical or different, are selected from among the radicals R and a hydrogen atom, or by the following formula (2a):

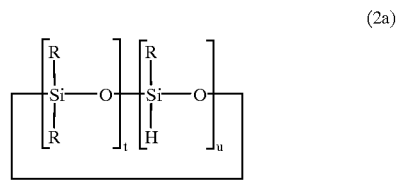

in which R, t and u are as defined above in respect of the formula (2).

A conventional hydrosilylation reaction is thus carried out on this SiH-containing derivative of formula (1a) or (2a), which reaction is conducted in the presence of a catalytically effective amount of a platinum catalyst, with an organic cinnamonitrile compound having the following formula (4a):

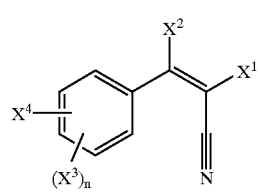

in which $X^1$, $X^2$, $X^3$, $X^4$ and n are as defined above in repect of for formula (4), except that one of the two radicals $X^1$ and $X^4$, instead of representing a divalent radical —Y— of formula (5) defined above, is, in this event, the corresponding unsaturated homologous monovalent radical having the following formula (5a):

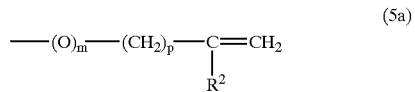

in which $R^2$, m and p are as defined above in respect of the formula (5).

Exemplary compounds of formula (4a) according to the present invention include, in particular:

(a) 2-Methylallyl 2-cyano-3,3-diphenylacrylate (b) Ethyl 3-(4-allyloxyphenyl)-2-cyanoacrylate (c) Ethyl 2-cyano[3-methoxy-4-(2-methylallyl-oxy) phenyl]acrylate (d) Ethyl 3-[4-allyloxy-3-methoxyphenyl]2-cyanoacrylate.

Suitable processes for the preparation of the compounds of formula (4a) are described, in particular, in FR-A-1,487, 593 and EP-A-0,430,023 and in U.S. Pat. No. 4,178,303, hereby expressly incorporated by reference. In particular, these compounds may be prepared by reacting para-allyloxybenzaldehyde with ethyl cyanoacrylate (so-called "Knoevenagel" reaction).

The platinum catalysts used to carry out the hydrosilylation reaction between the compounds of formula (1a) or (2a) above and the compound of formula (4a) above are well-known and widely described in the literature. Exemplary thereof are, in particular, the complexes of platinum and an organic compound described in U.S. Pat. Nos. 3,159,601, 3,159,602 and 3,220,972 and European Patent Applications EP-A-0,057,459, EP-A-0,188,978 and EP-A-0,190,530 and the complexes of platinum and vinyl organopolysiloxanes described in U.S. Pat. Nos. 3,419,593, 3,377,432 and 3,814, 730. To react the compounds of formula (1a) or (2a) with the compound of formulae (4a), an amount of platinum catalyst, calculated as weight of platinum metal, ranging from 5 to 600 ppm, preferably from 10 to 200 ppm, based on the weight of compounds of formula (1a) or (2a), is generally employed. The hydrosilylation reaction may be carried out in bulk or in a volatile organic solvent such as toluene, heptane, xylene, tetrahydrofuran or tetrachloroethylene. It is generally desirable to heat the reaction mixture to a temperature ranging from 60 to 120° C. for the period of time required for the reaction to be driven to completion. The compound of formula (1a) or (2a) may be added dropwise to the compound of formula (4a) in solution in an organic solvent containing the catalyst. The compound of formula (1a) or (2a) and the compound of formula (4a) may also be added simultaneously to a suspension of catalyst in an organic solvent. It is preferred to monitor that the reaction is complete by assaying the residual SiH using alcoholic potassium hydroxide, followed by removal of the solvent, for example by distillation under reduced pressure. The crude oil obtained may be purified, for example by cascading same through an absorbent column of silica.

As regards the preparation of the screening agents of triorganosilane type of formula (3) given above, the process may be carried out as indicated above, again by a hydrosilylation reaction, between a starting silane of formula (R')$_3$SiH (formula (3a), in which R' has the same definition as for the compound of formula (3)), and an organic cinnamonitrile derivative of formula (4a) defined above.

Another synethesis (Method 2) which is suitable for the preparation of the silicone screening agents of formulae (1) and (2), in the specific case where $X^2$ is hydrogen, comprises conducting a hydrosilylation reaction between a compound of formula (1a) or (2a), respectively, and an unsaturated formyl compound having the following formula (4b):

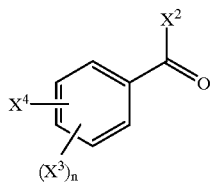

(4b)

in which $X^2$ is hydrogen, n and $X^3$ are as defined above in respect of formula (4), and $X^4$ is an unsaturated monovalent radical having the above formula (5a).

The product obtained after hydrosilylation is then reacted with a cyanoacetate or the malononitrile having the following formula (6):

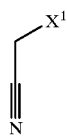

(6)

in which $X^1$ is a cyano radical or an alkoxycarbonyl radical $COOR^1$ in which $R^1$ is a linear or branched $C_1$–$C_{20}$ alkyl radical or a $C_2$–$C_{20}$ hydroxyalkyl radical, whereby the desired compound of formula (1) or (2) is obtained.

Also as indicated above, the compounds of formulae (1) to (3) above exhibit excellent intrinsic screening activity with respect to UV-A and UV-B ultraviolet radiation, depending upon the particular chemical structure thereof. By admixing compounds of different structure, namely, more specifically, by mixing compounds according to the invention displaying purely UV-A activity with products according to the invention displaying purely UV-B activity, it is thus possible to provide a composition which will display overall an exceptional sunscreen activity over the entire range of harmful UV (UV-A+UV-B), which is a considerable advantage. In addition, taking account of their highly liposoluble nature, the compounds of formulae (1) to (3) may be used in high concentrations, thereby imparting very high specific protection factors to the final compositions; moreover, they distribute themselves uniformly in standard cosmetic vehicles comprising at least one fatty phase or at least one cosmetically acceptable organic solvent, and may thus be applied to the skin or hair to form an effective protective film. Too, their cosmetic properties are very good, namely, in particular, compared with the silicone screening agents of the prior art, these products are less sticky and render the skin or hair softer.

Thus, the present invention also features cosmetic compositions comprising, in a cosmetically acceptable vehicle, carrier or diluent, preferably including at least one fatty phase or at least one organic solvent, an effective photoprotective amount of at least one compound of the above formulae (1) to (3).

The compounds of formulae (1) to (3) are advantageously present in proportions ranging from 0.1% to 20% by weight, and preferably from 0.5% to 10% by weight, relative to the total weight of the composition.

The cosmetic compositions of the invention may be used as compositions for protecting the human epidermis or hair against ultraviolet rays, as sunscreen compositions or as makeup products.

These compositions may, in particular, be in the form of a lotion, a thickened lotion, a gel, a cream, an ointment, a milk, a powder or a solid stick and may optionally be packaged as an aerosol, as a foam, a mousse or a spray.

They can contain the usual cosmetic adjuvants and additives, such as fats and fatty substances, organic solvents, silicones, thickeners, softeners, emollients, complementary sunscreens, anti-foaming agents, moisturizing or hydrating agents, fragrances and perfumes, preservatives, surfactants, fillers, sequestering agents, anionic, cationic, nonionic or amphoteric polymers or mixtures thereof, propellants, basifying or acidifying agents, colorants, dyes, pigments or nanopigments, in particular those designed to provide a complementary photoprotective effect by physically blocking out ultraviolet radiation, or any other ingredient customarily used in cosmetics, especially for the production of sunscreen compositions.

Exemplary of the organic solvents are the lower alcohols and polyols, such as ethanol, isopropanol, propylene glycol, glycerol and sorbitol.

The fats or fatty substances can comprise of an oil or wax or mixtures thereof, fatty acids, fatty acid esters, fatty alcohols, petrolatum, paraffin, lanolin, hydrogenated lanolin or acetylated lanolin. The oils may be selected from among animal, vegetable, mineral or synthetic oils and, in particular, hydrogenated palm oil, hydrogenated castor oil, liquid petrolatum, liquid paraffin, purcellin oil, volatile or non-volatile silicone oils, and isoparaffins.

When the cosmetic composition according to the invention are used for protecting the human epidermis against the deleterious or damaging effects of UV irradiation or as sunscreen compositions, they are advantageously formulated as a suspension or dispersion in solvents or fatty substances, or, alternatively, in the form of an emulsion (in particular of OW or W/O type, but preferably of O/W type) such as a cream or a milk, or of a vesicle dispersion, or as an ointment, a salve, a gel, a solid stick or an aerosol foam. The emulsions may additionally contain anionic, nonionic, cationic or amphoteric surface-active agents.

When the cosmetic compositions according to the invention are used for the photoprotection of the hair, they can be formulated as a shampoo, a lotion, a gel or rinse, to be applied before or after shampooing, before or after dyeing or bleaching, before, during or after permanent-waving or straightening of the hair, or as a styling or treatment lotion or gel, a blow-drying or hair-setting lotion or gel, a hair lacquer, a permanent-waving or hair-straightening composition, or a composition for dyeing or bleaching the hair.

When the cosmetic compositions according to the invention are used as makeup products for the eyelashes, the eyebrows, the skin or the hair, such as a skin-treatment cream, a foundation, a lipstick, an eye shadow, a blush, an eyeliner, a mascara or a coloring gel, they can be formulated in solid or pasty, anhydrous or aqueous form, such as oil-in-water or water-in-oil emulsions, suspensions or gels.

The cosmetic treatment of the skin or hair to protect same against the deleterious effects of ultraviolet radiation, in particular solar radiation, comprising topically applying to the skin or hair an effective amount of a sunscreen/cosmetic composition as described above, or of a compound of the above formulae (1) to (3).

In order to further illustrate the present invention and the advantages thereof, the following specific examples are given, it being understood that same are intended only as illustrative and in nowise limitative.

EXAMPLE 1

This example relates to the preparation (according to Method 1) of a compound in accordance with the present invention, having the structural formula:

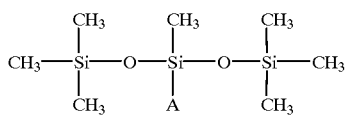

in which A is the radical:

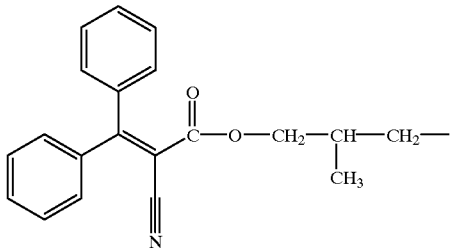

(this compound has formula (1) in which R=B=CH$_3$; r=0; s=1; n=0; X$^2$=phenyl; X$^4$=H; X$^1$=COO—Y— with, for Y: m=0, p=1 and R$^2$=CH$_3$).

(a) First stage:

Benzophenone (50 g; 0.274 mol), methallyl cyanoacetate (46 g; 0.33 mol), ammonium acetate (4.8 g), acetic acid (14.4 g) and heptane (110 ml) were introduced into a 250 ml reactor. The mixture was heated to reflux and the water was removed by distillation. 1.5 g of a 75/25 acetic acid/ammonium acetate mixture were added every hour. The stirring and heating were maintained for a total time of 24 hours. The mixture was cooled and poured into water, then extracted with dichloromethane. After washing with water and evaporation of the solvent, the product was purified on a column under pressure (eluent: heptane/ethyl acetate 95/5). The starting benzophenone (24 g) was recovered in the first fractions, and 28.5 g of 2-methylallyl 2-cyano-3,3-diphenylacrylate, having the following characteristics, was then obtained in the other fractions:

Pale yellow oil
Elemental analysis:
theoretical: C 79.19 H 5.65 N 4.62
found: C 79.57 H 5.59 N 4.51

(b) Second stare:

14.5 g of the compound obtained above and 30 ml of toluene were introduced into a reactor. The mixture was then heated to 80° C., under nitrogen. The hydrosilylation catalyst (complex containing 3–3.5% Pt in cyclovinylmethylsiloxane, marketed by Hüls under the trademark Petrarch PC085, 30 μl) was added, followed by dropwise addition, over 20 minutes, of 11.7 g of heptamethyltrisiloxane. After 3 hours at 80° C. under nitrogen, the reaction medium was concentrated and chromatography was carried out on silica under pressure (eluent: heptane/EtOAc 97/3). 9.5 g of the desired final compound, having the following characteristics, were thus obtained:

Pale yellow oil
Elemental analysis:
theoretical: C 61.67 H 7.48 N 2.66 Si 16.02
found: C 61.79 H 7.59 N 2.51 Si 15.89

The UV absorption characteristics (measured in ethanol) of this compound were as follows:

$\lambda_{max}$: 303 nm $\epsilon_{max}$: 11,950

This compound is thus a very effective sunscreen which is active in the UV-B range.

EXAMPLE 2

This example relates to the preparation (according to Method 2) of a compound in accordance with the present invention, having the stuctural formula:

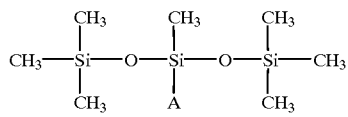

in which A is the radical:

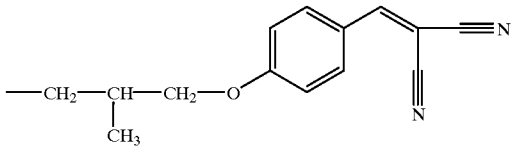

(this compound has formula (1) in which R=B=CH$_3$; r=0; s=1; X$^1$=cyano; X$^2$=H; n=0; X$^4$=—Y— with, for Y: p=m=1 and R$^2$=methyl).

(a) First stage:

17.62 g (0.1 mol) of 4-(2-methylallyloxy)-benzaldehyde and 50 ml of dry toluene were introduced into a reactor. The mixture was heated to 80° C., under nitrogen. The hydrosilylation catalyst (complex containing 3–3.5% Pt in cyclovinylmethylsiloxane, marketed by Hüls under the Trademark Petrarch PC085: 100 μl) was then added, followed by dropwise addition, over 20 minutes, of 24.47 g (0.11 mol) of heptamethyltrisiloxane. After 6 hours at 80° C. under nitrogen, the reaction medium was concentrated and chromatography was carried out on silica under pressure (eluent: heptane/EtOAc 98/2). 34.1 g (yield: 85%) of 3-[1,3,3,3-tetramethyl-1-(trimethylsilyl)oxydisiloxanyl]-2-methylpropyloxybenzaldehyde, having the following characteristics, were thus obtained:

Pale yellow oil
Boiling point=135°–141° C. at 0.1 mmHg (b) Second stage:

3.7 g of the compound obtained above, 2 ml of ethanol, 0.62 g of malononitrile and 2 drops of piperidine were introduced into a reactor. The mixture was maintained under stirring at ambient temperature for 4 hours. It was concentrated under vacuum and the product obtained was recrystallized from methanol, to provide the desired final compound, having the following characteristics:

White powder with yellow glints
M.p.: 41°–42° C.
Elemental analysis:
theoretical: C 56.46 H 7.67 N 6.27 Si 18.86
found: C 56.44 H 7.65 N 5.94 Si 18.55

The UV absorption characteristics (measured in ethanol) of this compound were as follows:

$\lambda_{max}$: 351 nm $\epsilon_{max}$: 32,400

This compound is thus a very effective sunscreen which is active in the UV-A range.

EXAMPLE 3

Following the same procedure as that given either in Example 1 or in Example 2, four other compounds in accordance with the present invention (Compounds A to C according to the process of Example 1; Compound D according to the process of Example 2), all having the general formula (1) and which were distinguished from each other by their silicone-containing skeleton or backbone and/or by the structure of the screening unit A, were prepared.

The structural formulae of these Compounds A to D were thus as follows:

Compound A:

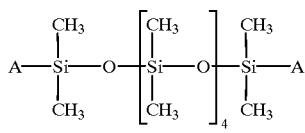

in which A is the radical:

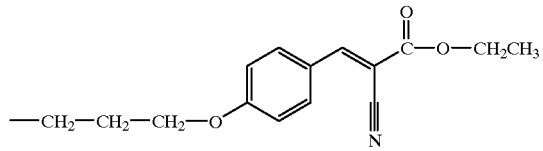

(this compound has formula (1) in which R=CH$_3$; B=A; r=4; s=0; n=0; X$^1$=COOR$^1$ with R$^1$=ethyl; X$^2$=H; X$^4$=—Y— with, for Y: m=p=1 and R$^2$=H).

Compound B:

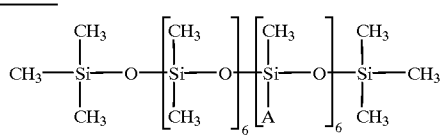

in which A is the radical:

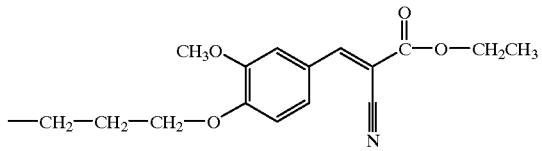

(this compound has formula (1) in which R=B=CH$_3$; r (mean value)=s (mean value)=6; X$^1$=COOR$^1$ with R$^1$=ethyl; X$^2$=H; n=1 and X$^3$=methoxy; X$^4$=—Y— with, for Y: m=p=1 and R$^2$=H).

Compound C:

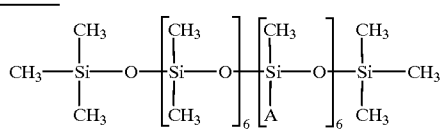

in which A is the radical:

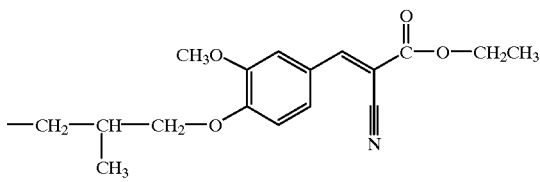

(this compound has formula (1) in which R=B=CH$_3$; r (mean value)=s (mean value)=6; X$^1$=COOR$^1$ with R$^1$=ethyl; X$^2$=H; n=1 and X$^3$=methoxy; X$^4$=—Y— with, for Y: m=p=1 and R$^2$=CH$_3$).

Compound D:

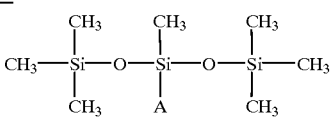

in which A is the radical:

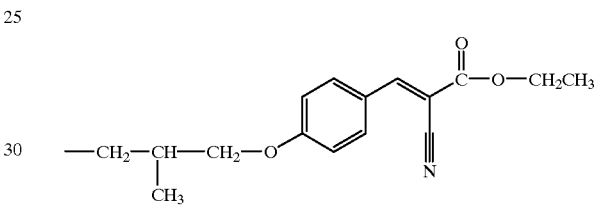

(this compound has formula (1) in which R=B=CH$_3$; r=0; s=1; X$^1$=COOR$^1$ with R$^1$=ethyl; X$^2$=H; n=0; X$^4$=—Y— with, for Y: m=p=1 and R$^2$=CH$_3$).

For each of the compounds A to D, the results obtained are reported in the following Table:

TABLE

| Compound | UV (solvent) $\lambda_{max}$ | $\epsilon_{max}$ | Elemental analysis (1) = calculated (2) = found |
|---|---|---|---|
| A | 348 nm (CHCl$_3$) | E1%* = 590 | (1): C 53.35 H 7.25 N 2.96 Si 17.82 (2): C 53.63 H 7.09 N 2.72 Si 17.54 |
| B | 364 nm (CHCl$_3$) | E1%* = 450 | $^1$H and $^{29}$Si NMR in agreement with the formula |
| C | 365 nm (CHCl$_3$) | E1%* = 265 | $^1$H and $^{29}$Si NMR in agreement with the formula |
| D | 344 nm (ethanol) | 31,000 | (1): C 55.94 H 7.96 N 2.84 Si 17.06 (2): C 55.97 H 7.92 N 2.78 Si 16.85 |

*E1% denotes the optical density of a 1% solution of compound.

*: E1% denotes the optical density of a 1% solution of compound.

The compounds A, B, C and D are thus very effectively as sunscreens which are active in the UV-A range.

EXAMPLE 4

A photoprotective/sunscreen formulation in accordance with the invention was prepared in the form of a sunscreen cream:

| | |
|---|---|
| (a) Compound of Example 1 | 5 g |
| (b) Mixture of cetylstearyl alcohol and cetylstearyl alcohol oxyethylenated with 33 mol of EO ("SINNOWAX AO" marketed by Henkel) | 7 g |
| (c) Non-self-emulsifiable mixture of glyceryl mono- and distearate | 2 g |
| (d) Cetyl alcohol | 1.5 g |
| (e) $C_{12}$–$C_{15}$ alkyl benzoate ("FINSOLV TN" marketed by Witco) | 20 g |
| (f) Polydimethylsiloxane | 1.5 g |
| (g) Glycerol | 17.5 g |
| (h) Fragrance, preservative | qs |
| (i) Water | qs 100 g |

This cream was formulated according to the standard techniques for the preparation of emulsions, by dissolving the screening agent in the fatty phase containing the emulsifying agents, heating this fatty phase to about 70°–80° C. and adding, with vigorous stirring, the water which had been heated to the same temperature. Stirring was maintained for 10 to 15 minutes and, after permitting this formulation to cool with moderate stirring, the fragrance and preservative were then finally added at about 40° C.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A cinnamonitrile-substituted polyorgano-siloxane/polyorganosilane compound having the formula (3):

(3)

in which the radicals R', which may be identical or different, are each a $C_1$–$C_8$ alkyl radical or a phenyl radical; and the radical A is a monovalent radical bonded directly to a silicon atom and which has the following formula (4):

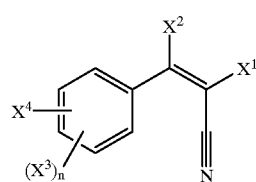

(4)

wherein $X^1$ is a cyano radical or an alkoxycarbonyl radical $COOR^1$ in which the radical $R^1$ is (i) a $C_1$–$C_{20}$ alkyl radical, (ii) a $C_2$–$C_{20}$ hydroxyalkyl radical, or (iii) a divalent radical —Y— having the following formula (5):

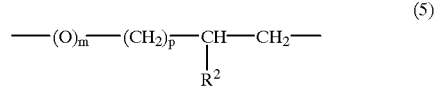

(5)

in which $R^2$ is a hydrogen atom or a $C_1$–$C_4$ alkyl radical, p is an integer ranging from 0 to 10, inclusive; m is 0 or 1; the —$CH_2$— endgroup is directly bonded to a silicon atom; $X^2$ is a hydrogen atom or an optionally substituted phenyl or $C_6$–$C_{10}$ aryl radical; n is an integer ranging from 0 to 2, inclusive; the radicals $X^3$, which may be identical or different, are each a $C_1$–$C_8$ alkyl radical or a $C_1$–$C_4$ alkoxy radical, with the proviso that, when the radicals $X^3$ are alkoxy radicals, two adjacent radicals $X^3$ (n=2) may together form an alkylidenedioxy group in which the alkylidene moiety contains 1 or 2 carbon atoms; and $X^4$ is a hydrogen atom or a divalent radical —Y—, with the proviso that, if $X^4$ is a hydrogen atom, then $X^1$ is necessarily a radical COOY in which m is zero.

2. A polyorganosiloxane/polyorganosilane compound as defined by claim 1, wherein formula (3), the radicals R' are methyl, ethyl, propyl, n-butyl, n-octyl or 2-ethylhexyl radicals.

3. A polyorganosiloxane/polyorganosilane compound as defined by claim 2, said radicals R' being methyl radicals.

4. A polyorganosiloxane/polyorganosilane compound as defined by claim 1, wherein the formula (3), $X^1$ is a cyano radical or a radical $COOR^1$ in which $R^1$ is a methyl or ethyl radical, or a radical —Y—.

5. A polyorganosiloxane/polyorganosilane compound as defined by claim 1, wherein the formula (3), $X^2$ is hydrogen or a phenyl radical.

6. A polyorganosiloxane/polyorganosilane compound as defined by claim 1, wherein the formula (3), $X^3$ is methoxy radical (n≠0) or is hydrogen (n=0).

7. A polyorganosiloxane/polyorganosilane compound as defined by claim 1, wherein the formula (3), a divalent radical —Y— is on the 4-position of the benzene ring.

8. A polyorganosiloxane/polyorganosilane compound as defined by claim 1, wherein the formula (3), in a divalent radical —Y—, p ranges from 1 to 3.

9. A polyorganosiloxane/polyorganosilane compound as defined by claim 1, wherein the formula (3), in a divalent radical —Y—, $R^2$ is hydrogen or a methyl radical.

10. A topically applicable sunscreen/cosmetic composition adopted for the photoprotection of human skin and/or hair, comprising a photoprotecting effective amount of a polyorganosiloxane/polyorganosilane compound as defined by claim 1, in a cosmetically acceptable vehicle, carrier or diluent therefor.

11. The sunscreen/cosmetic composition as defined by claim 10, said cosmetically acceptable vehicle, carrier or diluent comprising at least one fatty phase or at least one organic solvent.

12. The sunscreen/cosmetic composition as defined by claim 10, comprising an oil-in-water or water-in-oil emulsion.

13. The sunscreen/cosmetic composition as defined by claim 10, comprising from 0.1% to 20% by weight of said photoprotecting compound.

14. A method for protecting human skin and/or hair against the deleterious effects of ultraviolet irradiation, comprising topically applying thereto an effective amount of the sunscreen/cosmetic composition as defined by claim 10.

15. A method for protecting human skin and/or hair against the deleterious effects of solar radiation, comprising topically applying thereto an effective amount of the sunscreen/cosmetic composition as defined by claim 10.

* * * * *